United States Patent [19]

Uzuyama et al.

[11] Patent Number: 5,416,819
[45] Date of Patent: May 16, 1995

[54] DIGITAL X-RAY RADIOGRAPHIC APPARATUS

[75] Inventors: Kazuhiro Uzuyama, Kyoto; Hidefumi Suzuki, Osaka; Takeshi Ozaki, Kyoto; Tatsuhiro Mori, Hirakata; Hiroshi Sawada, Kyoto; Yusuke Miura, Kyoto; Kazuhiro Mori, Kyoto, all of Japan

[73] Assignee: Shimadzu Corporation, Kyoto, Japan

[21] Appl. No.: 154,115

[22] Filed: Nov. 18, 1993

[30] Foreign Application Priority Data

Nov. 27, 1992 [JP] Japan .................. 4-341686

[51] Int. Cl.$^6$ .................................. A61B 6/00
[52] U.S. Cl. ........................ 378/116; 378/98.5; 378/114
[58] Field of Search ............ 378/62, 98, 98.2, 98.5, 378/98.12, 114, 115, 116

[56] References Cited

U.S. PATENT DOCUMENTS

| | | | |
|---|---|---|---|
| 4,674,107 | 6/1987 | Urban et al. | 378/98.5 |
| 4,680,628 | 7/1987 | Wojcik et al. | 378/98.2 |
| 4,730,212 | 3/1988 | Wojcik et al. | 378/98.2 |
| 4,975,937 | 12/1990 | Horton et al. | 378/114 |
| 4,993,404 | 2/1991 | Lane | 378/114 |
| 5,022,063 | 6/1991 | Yokouchi et al. | 378/116 |
| 5,091,926 | 2/1992 | Horton et al. | 378/114 |

*Primary Examiner*—David P. Porta
*Attorney, Agent, or Firm*—Nikaido, Marmelstein, Murray & Oram

[57] ABSTRACT

X-ray penetration images picked up by an X-ray penetrating device are supplied to an image processor, and stored in a magnetic disk unit as radiographic image data. The radiographic image data are reproduced on a reproduced image display monitor installed in an examination room. The examination room further includes a fluoroscopic image display monitor for selectively displaying the fluoroscopic images and menus. The menus include functions to select radiographic image data for reproduction on the reproduced image display monitor and to select a display mode. The functions shown on the menus may be selected and instructed by operating a joystick. During a procedure of interventional radiology, an operator operates the joystick to select and instruct desired radiographic image data to be reproduced. A display mode for enlarging reproduced images may be selected as necessary.

19 Claims, 13 Drawing Sheets

DIGITAL X-RAY RADIOGRAPHIC APPARATUS

BACKGROUND OF THE INVENTION

(1) Field of the Invention

This invention relates to digital X-ray radiographic apparatus for use in interventional radiology (IVR), for example, and having a function to reproduce radiographic image data. More particularly, the invention relates to a device for selecting radiographic image data for reproduction.

(2) Description of the Related Art

The digital radiographic apparatus digitalizes, for example, X-ray penetration images of visualized blood vessels obtained from various directions of an examinee. Resulting data are stored in a storage medium such as a magnetic disk, so that the X-ray penetration images (radiographic image data) may be reproduced when desired.

IVR is a therapeutic procedure in which an operator (doctor) treats, with a catheter inserted into a patient's body, clogging of a blood vessel, cancer cells or the like found through angiography. In the IVR procedure, a comparison is made between fluoroscopic images currently obtained through angiography and X-ray penetration images (radiographic image data) obtained through angiography in advance. It is therefore necessary to reproduce, during the IVR procedure, desired radiographic image data in the examination room where the operator is working. Such data are selected from the radiographic image data stored in the storage medium of the digital radiographic apparatus.

Thus, the digital radiographic apparatus includes a monitor installed in the examination room where the operator works, for reproducing and displaying the radiographic image data. Conventionally, an engineer carries out an operation on a control console installed in a control room separate from the examination room to reproduce the radiographic image data. During the IVR procedure, the operator gives verbal instructions through an intercom or the like to the engineer for reproduction of the radiographic image data the operator desires.

Preferably, during the IVR procedure, the desired radiographic image data should be reproduced immediately. With the conventional apparatus, however, the desired data are not reproduced immediately since the reproduction is done through the engineer. This and other aspects of the conventional apparatus constitute a disadvantage in operating efficiency.

SUMMARY OF THE INVENTION

Having regard to the state of the art noted above, the object of this invention is to provide a digital X-ray radiographic apparatus for enabling radiographic image data desired by an operator to be reproduced immediately and efficiently.

The above object is fulfilled, according to a first aspect of this invention, by a digital X-ray radiographic apparatus for digitalizing and collecting X-ray penetration images of an examinee, and reproducing the X-ray penetration images collected, the apparatus comprising:

an X-ray penetrating device for obtaining the X-ray penetration images from the examinee;

a signal converting device for digitalizing the X-ray penetration images received from the X-ray penetrating device;

a storage device for storing the X-ray penetration images digitalized by the signal converting device;

a reproduced image display monitor installed in an examination room along with the X-ray penetrating device, for reproducing and displaying the X-ray penetration images (hereinafter referred to as "radiographic image data") digitalized and stored in the storage device;

a fluoroscopic image display monitor installed in the examination room for displaying fluoroscopic images being picked up by the X-ray penetrating device;

a menu generating/displaying device for generating a menu including at least a function to select radiographic image data to be reproduced and displayed on the reproduced image display monitor, and causing the menu to be displayed on the fluoroscopic image display monitor;

a selecting and instructing device installed in the examination room for selecting and instructing functions shown on the menu;

a display switching device for switching the fluoroscopic image display monitor between a state for displaying the fluoroscopic images being picked up by the X-ray penetrating device and a state for displaying the menu generated by the menu generating/displaying device; and a control device responsive to instructions received from the selecting and instructing device for causing the radiographic image data to be reproduced and displayed on the reproduced image display monitor.

An apparatus according to a second aspect of this invention comprises a superimposing device, in place of the display switching device, for causing the menu to be displayed on the fluoroscopic image display monitor in superimposition on the fluoroscopic images being picked up by the X-ray penetrating device.

Further, an apparatus according to a third aspect of this invention dispenses with the display switching device in the first-mentioned apparatus, and includes a menu display monitor besides the fluoroscopic image display monitor. The menu generated by the menu generating/displaying device is displayed on the menu display monitor.

With these apparatus, radiographic image data to be reproduced may be selected and instructed by operating the selecting and instructing device installed in the examination room. Thus, the operator himself or herself can carry out the selecting and instructing operation. As a result, the radiographic image data desired by the operator during an IVR procedure may be reproduced immediately. The menu showing the control functions performed in response to operation of the selecting and instructing device is displayed on the monitor (on the fluoroscopic image display monitor in the apparatus according to the first and second aspects of this invention, or on the menu display monitor in the apparatus according to the third aspect of the invention) installed in the examination room. The operator may refer to the menu while observing the radiographic image data reproduced, and operate the selecting and instructing device to effect the selecting and instructing operation. This promotes operating efficiency in selecting and instructing radiographic image data to be reproduced.

BRIEF DESCRIPTION OF THE DRAWINGS

For the purpose of illustrating the invention, there are shown in the drawings several forms which are presently preferred, it being understood, however, that the invention is not limited to the precise arrangements and instrumentalities shown.

DETAILED DESCRIPTION OF THE PREFERRED EMBODIMENTS

Preferred embodiments of this invention will be described in detail hereinafter with reference to the drawings.

First Embodiment

Figure 1:
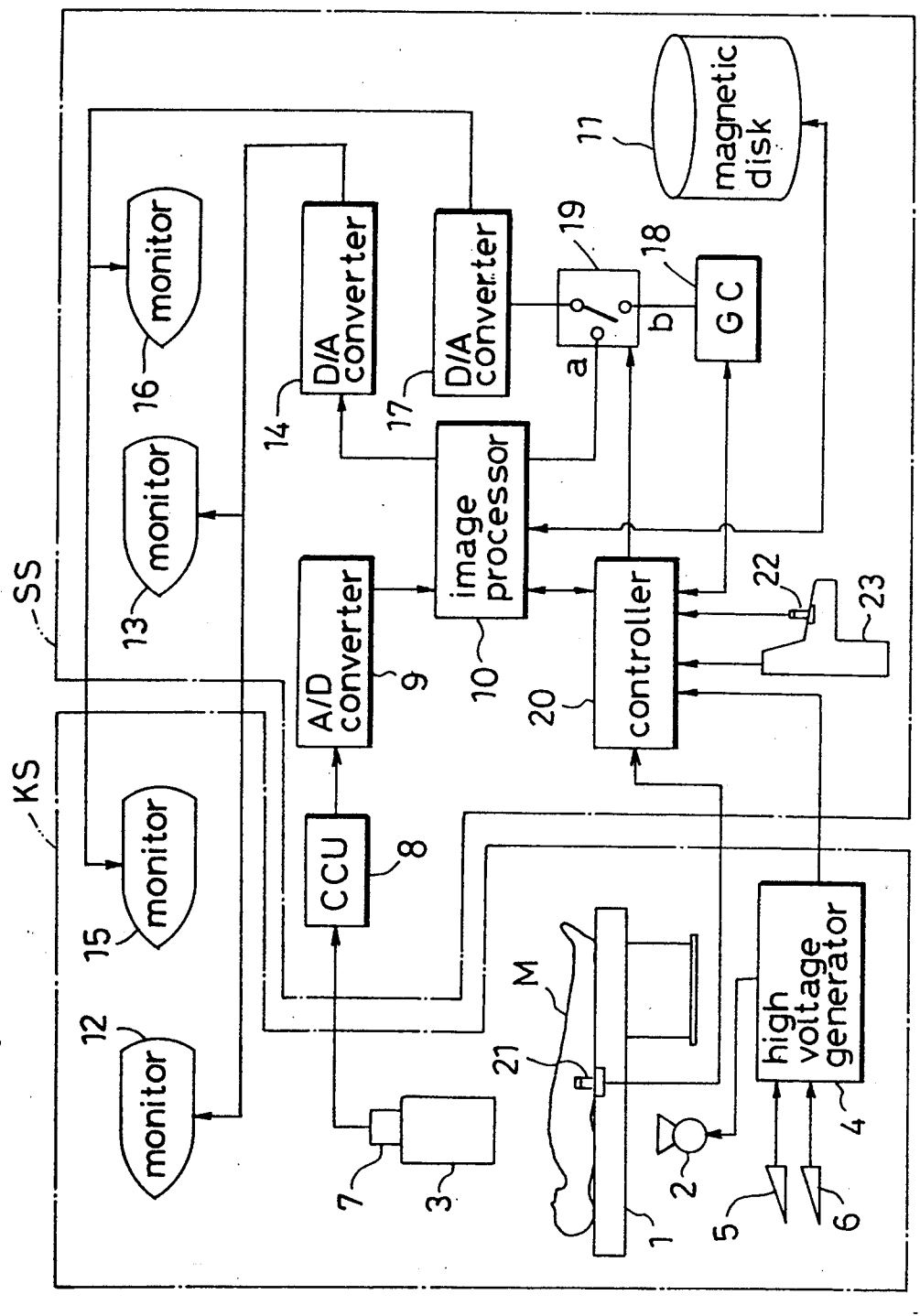
FIG. 1 is a block diagram showing an outline of a digital radiographic apparatus in a first embodiment of this invention.

FIG. 1 is a block diagram showing an outline of a digital radiographic apparatus in a first embodiment of this invention.

Numeral 1 in FIG. 1 denotes a bed for supporting an examinee M lying thereon. An X-ray tube 2 and an image intensifier unit 3 are opposed to each other across the examinee M lying on the bed 1.

A high voltage generator 4 is connected to the X-ray tube 2. When an operator steps on a photographing foot switch 5 or a monitoring foot switch 6 arranged adjacent the bed 1, the high voltage generator 4 applies a high current to the X-ray tube 2 to irradiate the examinee M with X-rays.

A television camera 7 is connected to the image intensifier unit 3. The X-rays having penetrated the examinee M are converted and intensified into visible light by the image intensifier unit 3, and picked up by the television camera 7. A CCU (camera controller) 8 is connected to the television camera 7. The CCU 8 processes, e.g. amplifies, a signal outputted from the television camera 7. An output signal of the CCU 8 is converted to a digital signal by an A/D (analog-to-digital) converter 9 to be supplied to an image processor 10.

The X-ray tube 2 and image intensifier unit 3, arranged in the opposed relationship, are movable along and around the body axis of the examinee M to obtain X-ray penetration images from various directions of the examinee M. The X-ray tube 2 and image intensifier unit 3 (including the television camera 7) may be moved by the operator manually or through a controller, not shown.

The photographing foot switch 5 is an instruction switch for causing the X-ray penetration images obtained as above to be stored in a magnetic disk unit 11 (i.e. X-ray photography) as described later. The monitoring foot switch 6 is an instruction switch for causing the fluoroscopic images being obtained to be shown on fluoroscopic image display monitors 15 and 16 (i.e. X-ray monitoring) as described later.

The components referenced 1 through 8 constitute an X-ray penetrating device of this invention. The A/D converter 9 corresponds to a signal converting device of this invention.

The image processor 10 carries out filtering processes on the digital signal supplied thereto, such as for reducing noise and defining edges. The magnetic disk unit 11 is connected to the image processor 10 for recording and collecting the X-ray penetration images. This magnetic disk unit 11 corresponds to a storage device of this invention.

Further, in order to reproduce and present the X-ray penetration images (radiographic image data) stored in the magnetic disk unit 11 on reproduced image display monitors 12 and 13, a D/A (digital-to-analog) converter 14 is connected to the image processor 10 for converting the radiographic image data in the form of digital signals to analog signals.

The reproduced image display monitor 12 corresponds to a reproduced image display monitor of this invention installed in an examination room. The reproduced image display monitor 13 corresponds to a control room reproduced image display monitor of this invention installed in a control room.

Output data (fluoroscopic image display data) of the image processor 10 is inputted to an input terminal "a" of a switch 19. The switch 19 has another input terminal "b" for receiving output data (menu display data) from a GC (graphic controller) 18 for generating menu representations described later.

The switch 19 has an output terminal connected to a D/A converter 17. The digital data received through a selected one of the input terminals "a" and "b" is converted to an analog signal by the D/A converter 17 to be displayed on the fluoroscopic image display monitors 15 and 16. The switch 19 is operable by a controller 20 to select the input terminal "a" or "b", depending on whether the operator depresses the monitoring foot switch 6 or not.

That is, when the operator depresses the monitoring foot switch 6, the D/A converter 17 is connected to the input terminal "a", and thus to the image processor 10. As a result, the fluoroscopic images currently obtained from the examinee M are shown on the fluoroscopic image display monitors 15 and 16. On the other hand, when the operator releases the monitoring foot switch 6, the D/A converter 17 is connected to the input terminal "b", and thus to the GC 18, whereby the menus are shown on the fluoroscopic image display monitors 15 and 16.

The GC 18 corresponds to a menu generating/displaying device of this invention. The switch 19 corresponds to a display switching device of this invention. The fluoroscopic image display monitor 15 corresponds to a fluoroscopic image display monitor of this invention installed in the examination room. The fluoroscopic image display monitor 16 corresponds to a control room menu display monitor of this invention installed in the control room.

Figure 2A:
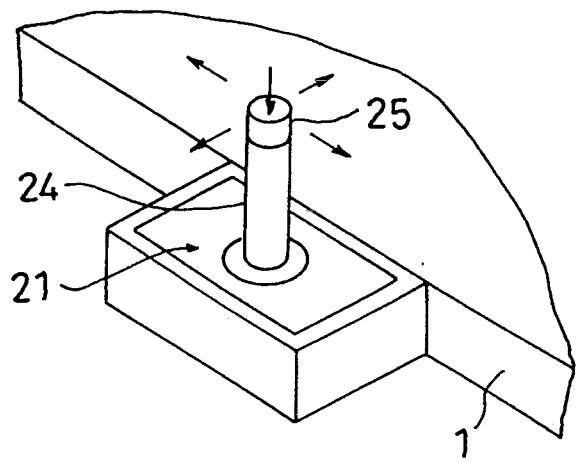
FIGS. 2A and 2B are perspective views of joysticks each having a pushbutton.
Figure 2B:
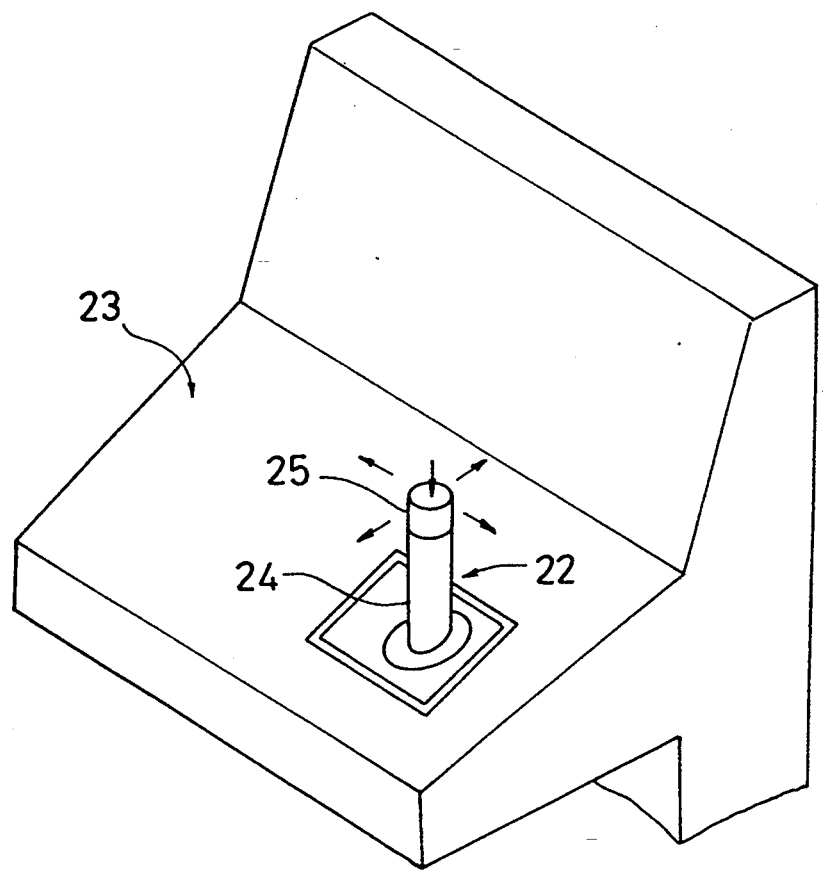

Numeral 21 denotes a joystick with a pushbutton which, as shown in FIG. 2A, is disposed on one side of the bed 1 for use by the operator. Numeral 22 denotes a joystick with a pushbutton which, as shown in FIG. 2B, is attached to a control console 23 for use by an engineer. Each of these joysticks 21 and 22 includes a lever 24 rockable crosswise and a button 25 depressable to select radiographic image data as described later.

The joystick 21 used by the operator corresponds to a selecting and instructing device of this invention installed in the examination room. The joystick 22 used by the engineer corresponds to a control room selecting and instructing device of this invention installed in the control room.

The joystick 21 in particular may be used with a sterilized cover placed thereon for the sake of sanitation. However, such a sterilized cover is not obstructive to the selecting and instructing operation since the joystick 21 is operable simply by rocking the lever 24 crosswise and pressing the button 25.

The control console 23 is used to set control data and the like to the controller 20 as described later. The control console 23 is used by the engineer.

The entire apparatus is operable under control of the controller 20. For example, the controller 20 instructs the image processor 10 to reproduce radiographic image data in response to operation of the switch 19 based on a state of the monitoring foot switch 6 as described above (the state of the monitoring foot switch 6 being transmitted through the high voltage generator 4) or operation of the joystick 21 or 22. The controller 20, image processor 10 and GC 18 include, for example, a CPU (central processing unit), a CPU memory and an external storage (such as a hard disk or a flexible disk). The external storage stores processing sequences (programs) executed by the respective components. Upon start of the apparatus, these programs are loaded into the CPU memory for execution by the CPU. The controller 20 corresponds to a control device of this invention.

In FIG. 1, reference KS denotes the examination room where the operator works, and the components bounded by reference KS are arranged in the examination room. Reference SS denotes the control room where the engineer works, and the components bounded by reference KS are arranged in the control room.

Operations of the apparatus having the above construction will be described hereinafter.

Operations for X-ray photography will be described first.

In X-ray photography, an ID (identification code) of the examinee M is set through the control console 23 or the like, and inputted to the controller 20. Next, the operator adjusts an angular relationship between the examinee M and the X-ray tube 2 and image intensifier unit 3. Information relating to the angular relationship, e.g. "RAO 30°" (the X-ray tube 2 being inclined 30° rightward with respect to the body axis of examinee M)" or "LAO 30° (the X-ray tube 2 being inclined 30° leftward with respect to the body axis of examinee M)", is set through the control console 3 and inputted to the controller 20. Alternatively, such information relating to the angular relationship may be transmitted to the controller 20 from a control unit of an X-ray tube and image intensifier holding device not shown. The ID and the information relating to the angular relationship inputted to the controller 20 are applied to the image processor 10.

Then, the operator steps on the photographing foot switch 5 to cause the X-ray tube 2 to irradiate the examinee M with X-rays. The X-rays having penetrated the examinee M are transmitted through the image intensifier unit 3, television camera 7, CCU 8 and A/D converter 9 to be supplied in digitalized form to the image processor 10. The image processor 10 writes the radiographic image data into the magnetic disk unit 11, and at the same time transmits the data through the D/A converter 14 to the reproduced image display monitors 12 and 13 for display.

While the photographing foot switch 5 is depressed, the radiographic image data are successively stored (collected) in the magnetic disk unit 11 and displayed on the reproduced image display monitors 12 and 13 at a predetermined speed. Where, for example, the television camera 7 has 525 scan lines in the vertical direction and the image processor 10 converts them into 512×512 pixels, the radiographic image data are collected in the magnetic disk unit 11 and displayed on the reproduced image display monitors 12 and 13 at the rate of 60 frames per second (60 frames of radiographic image data in one second). Where the television camera 7 has 1,024 scan lines in the vertical direction and the image processor 10 converts them into 1,024×1,024 pixels, the radiographic image data are stored and displayed at the rate of 30 frames per second. The speed at which the radiographic image data are collected is referred to as a collecting speed, which is dependent on the number of scan lines of the television camera 7 and the number of pixel matrices converted by the image processor 10.

Figure 3:
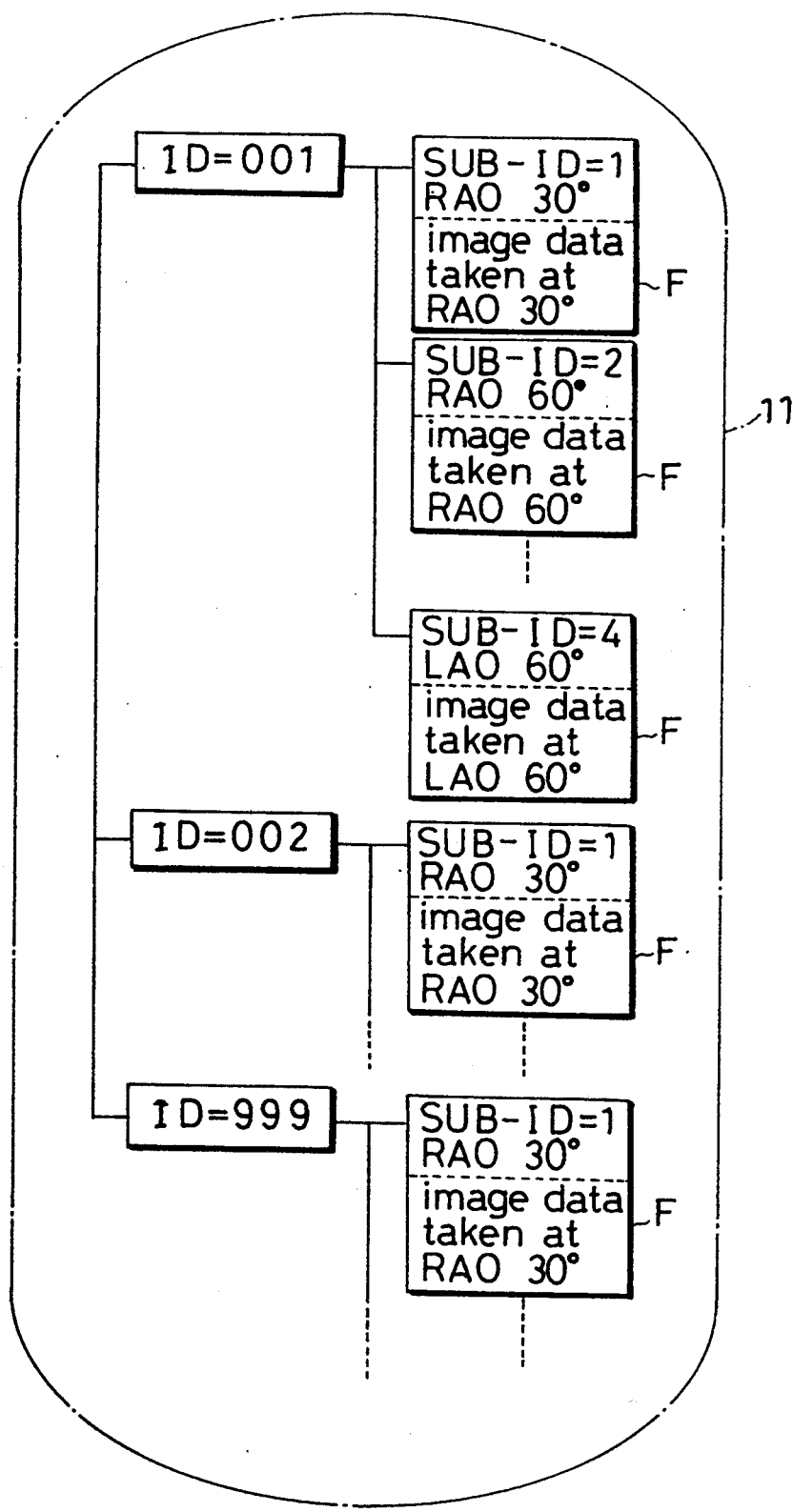
FIG. 3 is a view schematically showing management of files collected in a magnetic disk unit.

The magnetic disk unit 11 stores radiographic image data collected in one operation (i.e. collected over a period of time from depression to release of the photographing foot switch 5) as one file. In angiographic photography, for example, the magnetic disk unit 11 stores, as one file, numerous frames of radiographic image data showing a process of a contrast material introduced into the examinee M gradually filling blood vessels. Each file includes an identification number (SUB-ID) and information relating to an angular relationship at a photographing time (such as "RAO30°") applied from the image processor 10. Such files are grouped under each ID. Thus, as shown in FIG. 3, a plurality of files F stored in the magnetic disk unit 11 are classified according to IDs (examines M), each file containing radiographic image data obtained by varying the angle of the X-ray tube 2 and the like.

When the photographing foot switch 5 is released, i.e. when a photographing operation for one file is completed, the controller 20 causes the radiographic image data just collected in a file to be displayed on the reproduced image display monitors 12 and 13 cyclically at the collecting speed. A reproducing mode may be selected from a second menu described later, to cyclically display these radiographic image data and other data previously collected and stored in a plurality of files. The reproducing speed may be varied by operating the joystick 21 or 22 as described later.

Figure 4:
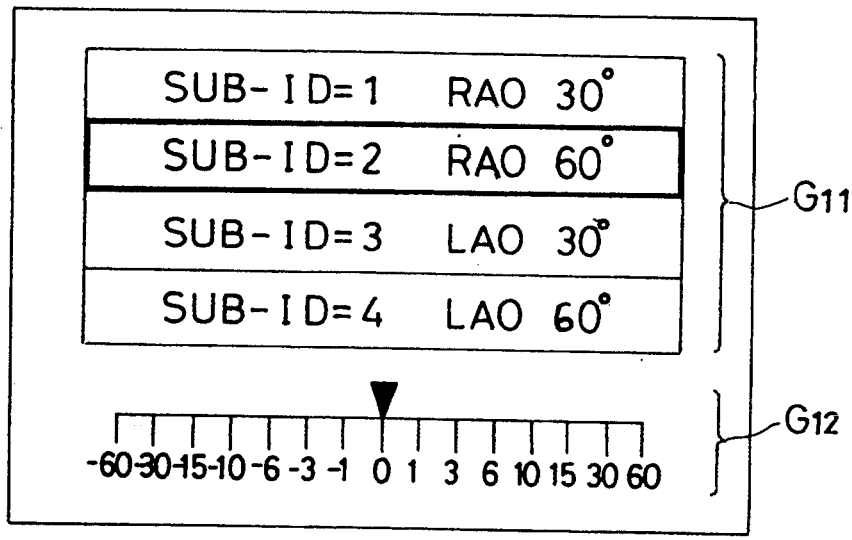
FIG. 4 is a view showing a first menu.

During the above process, the monitoring foot switch 6 remains out of operation, and therefore the input terminal "b" of the switch 18 is selected. Consequently, a first menu, as shown in FIG. 4, generated by the GC 18 is displayed on the fluoroscopic image display monitors 15 and 16. This screen shows mainly information regarding reproducing conditions of the radiographic image data currently displayed (reproduced) on the reproduced image display monitors 12 and 13. A portion G11 of the screen shows a list of files already photographed (including the file just photographed) of the examinee M (the same ID), with an indication (in a bold frame in FIG. 4) of the file currently reproduced on the reproduced image display monitors 12 and 13. A portion G12 shows a reproducing speed currently selected, with a numeral indicated by the pointer representing the current reproducing speed. Numeral "0" means zero reproducing speed, i.e. a still condition for showing still pictures. The plus numerals show numbers of frames advanced in one second for reproduction. When the data are reproduced at the collecting speed, for example, the pointer indicates "60 (60 frames per second)". The minus numerals show numbers of frames moved backward in one second for reproduction. The state of displaying the first menu is called herein "DISPLAY MODE".

In this state, the joysticks 21 and 22 are operable to produce the following effects:

(1) When the button 25 is pressed during a dynamic reproduction (at a reproducing speed other than "0"), the reproducing speed is set to "0" to establish the still condition.

(2) When the button 25 is pressed in the still condition, the screen is switched to a second menu described later, unless the monitoring foot switch 6 is depressed (i.e. only when the first menu is displayed).

(3) When, in the still condition, the lever 24 is inclined leftward and released at once, the radiographic image data in a preceding frame is displayed. When, in the still condition, the lever 24 is inclined rightward and released at once, the radiographic image data in a succeeding frame is displayed.

(4) When the lever 24 is maintained in a leftward inclined position, the reproducing speed is shifted from right to left in the portion G12 of the first menu. A reproducing speed indicated by the pointer may be selected. When the lever 24 is maintained in a rightward inclined position, the reproducing speed is shifted from left to right in the portion G12 of the first menu. Again, a reproducing speed indicated by the pointer may be selected.

(5) By rocking the lever 24 backward or forward, different files may be selected for reproduction. When the lever 24 is rocked backward or forward, the bold frame in the portion G11 of the first menu is shifted vertically. A reference image of a file marked by the bold frame may be displayed in still condition on the reproduced image display monitors 12 and 13.

The reference image is a radiographic image in a frame representative of each file. For example, a radiographic image in a frame obtained a predetermined time after start of a radiographic operation for one file is employed as the reference image. The above predetermined time corresponds, for example, to the time at which a contrast material injected into the examinee M fills a target site. This predetermined time is set in advance through the control console 23, and applied to the image processor 10 via the controller 20. Based on the predetermined time, the image processor 10 determines a reference image within the file. The reference image may be changed (re-registered) on the second menu described later. After a change of files, the file containing the reference image displayed in still condition is displayed cyclically at the collecting speed only when the lever 24 is inclined right or left ((3) or (4) above).

The first menu disappears when the monitoring foot switch 6 is depressed to display fluoroscopic images for observation on the fluoroscopic image display monitors 15 and 16. Even in this state, the operations other than operation (2) of the joystick 21 or 22 are accepted as valid. That is, the first menu shows the operations of the joystick 21 or 22 by way of guidance. However, the first menu must be displayed as above when calling the second menu described later (operation (2)). Further, the second menu must be displayed when the joystick 21 or 22 is operated in relation to the second menu. That is, the second menu shows jobs that can be done using the joystick 21 or 22 (e.g. selection of a display mode).

The second menu called by operating the joystick 21 or 22 as in operation (2) above will be described next with reference to FIG. 5.

Figure 5:
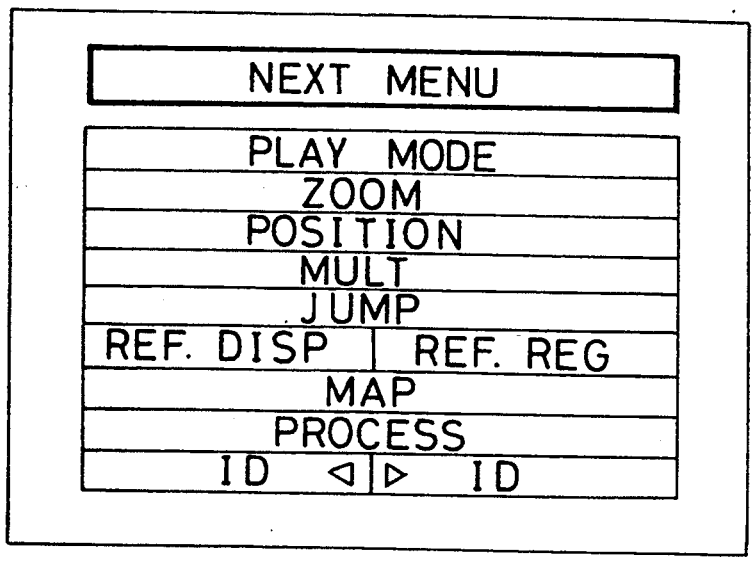
FIG. 5 is a view showing a second menu.

As shown in FIG. 5, the second menu shows a list of functions set out hereunder. A bold frame is movable from function to function on the second menu by rocking the joystick 21 or 22 crosswise, and a function marked by the bold frame may be selected by pressing the button 25.

(A) "NEXT MENU" is for returning to the first menu.

(B) "PLAY MODE" sets a reproducing mode when "DISPLAY MODE" is selected. By operating the lever 24 of the joystick 21 or 22 backward or forward after selecting this function, reproducing modes described hereinbelow successively appear in the position of "PLAY MODE" in FIG. 5. A desired reproducing mode may be selected by pressing the button of the joystick 21 or 22.

(a) "FAST FORWARD"

Figure 6:
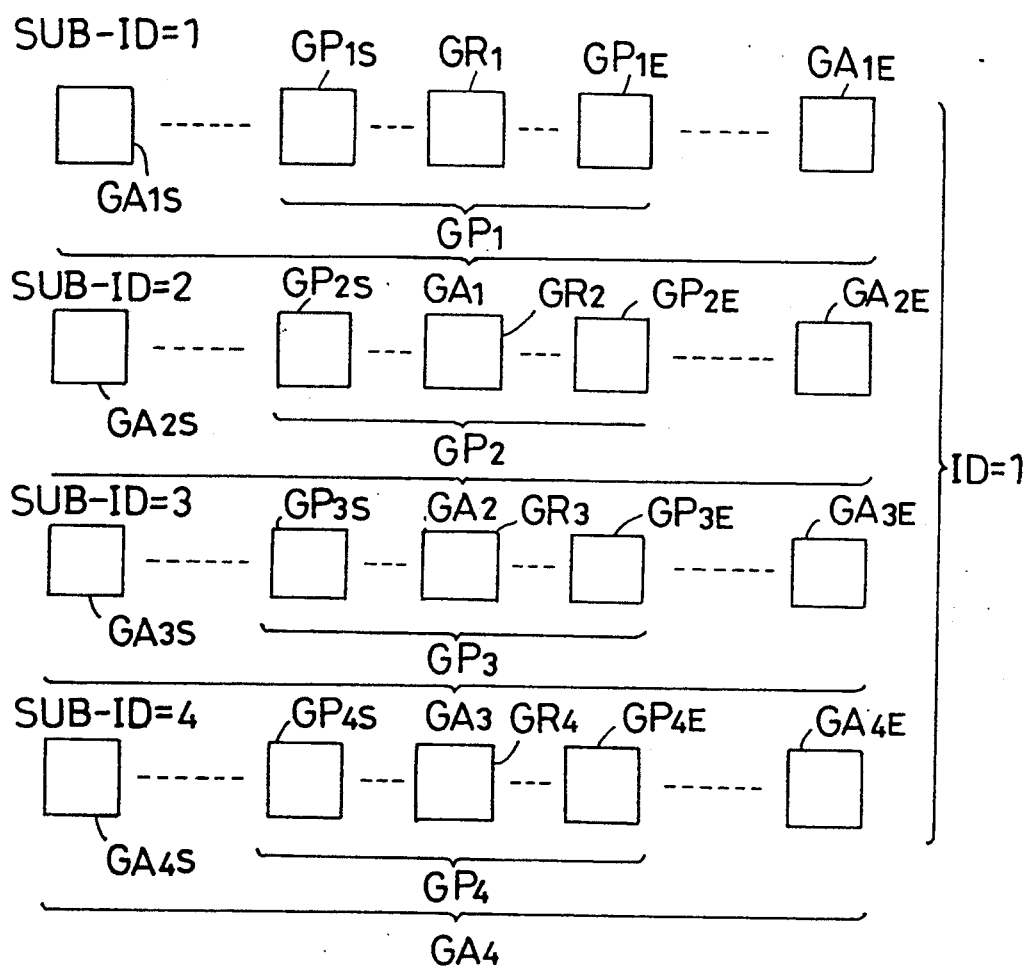
FIG. 6 is an explanatory view of a reproducing mode.

The radiographic image data obtained over a predetermined period of several seconds, with the reference image in the middle, of each file successively appear at the collecting speed, in the ascending order of the files with the same ID. Assume that ID=1 has four files SUB-ID=1 to 4 as shown in FIG. 6, for example. In this case, radiographic image data $GP_{1S}$ to $GP_{1E}$ obtained over the predetermined period of several seconds, with the reference image $GR_1$ in the middle, of file SUB-ID=1 are first reproduced and displayed at the collecting speed. It is to be noted that radiographic image data $GP_{1E}$ is a data obtained after radiographic image data $GP_{1S}$. Subsequently, images $GP_{2S}$ to $GP_{2E}$ of file SUB-ID=2 are reproduced and displayed at the collecting speed. Then, similarly, images $GP_3$ of file SUB-ID=3 and images $GP_4$ of file SUB-ID=4 are reproduced and displayed successively. After radiographic image data $GP_{4E}$ of file SUB-ID=4, radiographic image data $GP_{1S}$ to $GP_{1E}$ of file SUB-ID=1 are reproduced and displayed at the collecting speed again. The other image data appear similarly in cycles. The predetermined period of several minutes noted above is set through the control console 23 in advance.

(b) "FORWARD"

All radiographic image data forming the respective files are successively displayed at the collecting speed, in the ascending order of the files with the same ID. In the example shown in FIG. 6, images $GA_{1S}$ to $GA_{1E}$ of file SUB-ID=1 are first reproduced and displayed at the collecting speed. It is to be noted that image data $GA_{1S}$ is the first data obtained in collecting the radiographic image data for this file (i.e. the radiographic image data obtained at start of the radiographic process), while data $GA_{1E}$ is the radiographic image data obtained at finish of the radiographic process. Subsequently, image data $GA_2$, $GA_3$ and $GA_4$ of files SUB-ID=2, 3 and 4 are reproduced and displayed. After radiographic image data $GA_{4E}$ of file SUB-ID=4, radiographic image data $GA_{1S}$ to $GA_{1E}$ of file SUB-ID=1 are reproduced and displayed at the collecting speed again. The other image data appear similarly in cycles.

(c) "PLAY"

All radiographic image data constituting a single file are displayed cyclically at a predetermined reproducing speed. In the example shown in FIG. 6, when file SUB-ID=1 is selected for reproduction, images $GA_{1S}$ to $GA_{1E}$ are reproduced and displayed at the reproducing speed. After image $GA_{1E}$, images $GA_{1S}$ to $GA_{1E}$ are reproduced and displayed at the reproducing speed again. The reproducing speed is selected in the portion G12 of the first menu. A file may be selected for reproduction by operating the joystick 21 or 22 with reference to the portion G12 of the first menu, or by "MULT" or "JUMP" function as described later.

(d) "FAST PLAY"

The radiographic image data obtained over the predetermined period of several seconds, with the reference image in the middle, of a single file are displayed cyclically at a predetermined reproducing speed. The above predetermined period of several seconds is set through the control console 23 in advance. The reproducing speed and a file to be reproduced may be selected as for "PLAY" described above.

(e) "REVERSE"

This is the same as (b) above excepting that here the data are reproduced in the descending order of the files. In the example shown in FIG. 6, images $GA_{4S}$ to $GA_{4E}$ of file SUB-ID=4 are first reproduced and displayed at the collecting speed. Next, image data $GA_{3S}$ to $GA_{3E}$ of file SUB-ID=3 are reproduced at the collecting speed. Subsequently, $GA_2$ and $GA_1$ of files SUB-ID=2 and 1 are reproduced and displayed in succession. After image data $GA_1$ of file SUB-ID=1, image data $GA_4$ of file SUB-ID=4 are reproduced and displayed again.

(f) "FAST REVERSE"

This is the same as (a) above excepting that here the data are reproduced in the descending order of the files.

Figure 7:
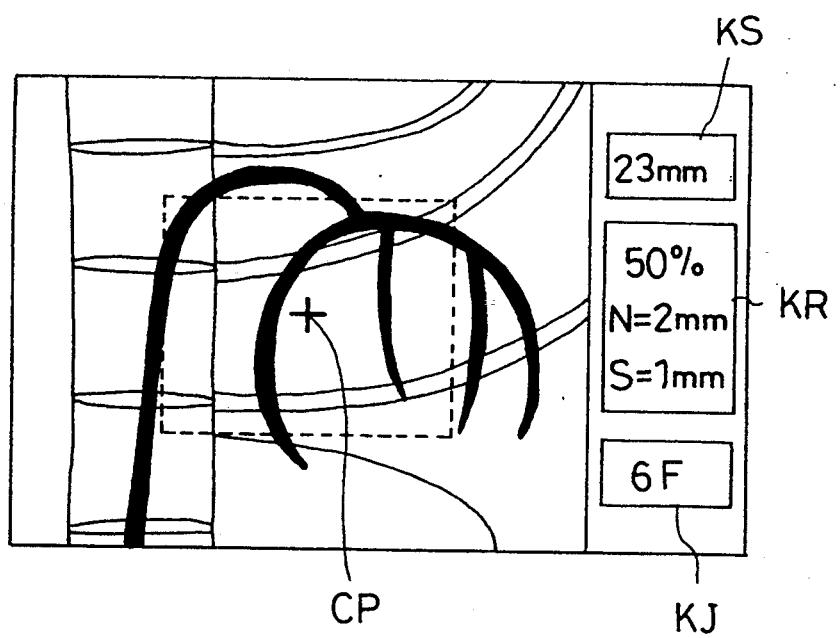
FIG. 7 is an explanatory view of a "ZOOM" function.

(C) "ZOOM" is a process of magnifying reproduced radiographic image data twice. When this is selected by operating the joystick 21 or 22, image data is enlarged twice, around a central position of the image data. As shown in FIG. 7, for example, a region enclosed by a dotted line around a central position CP of radiographic image data is enlarged twice on the reproduced image display monitors 12 and 13.

Figure 8:
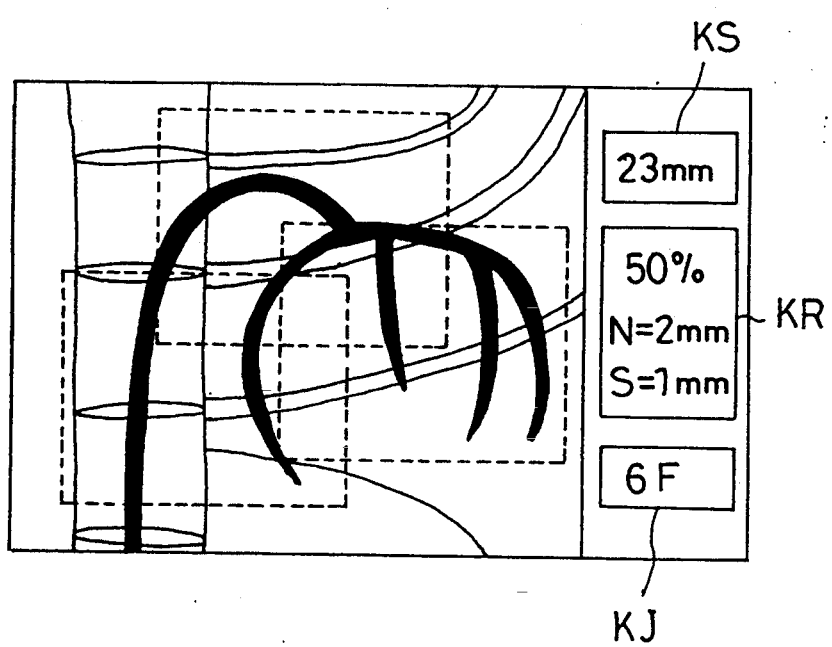
FIG. 8 is an explanatory view of a "POSITION" function.

(D) "POSITION" is a process of shifting the position enlarged by "ZOOM" above. The center of the enlarged image may be shifted by operating the joystick 21 or 22 to select this function and then rocking the lever 24 of the joystick 21 or 22 crosswise. As shown in FIG. 8, the enlarged region (enclosed in a dotted line) may be moved up and down and right and left by rocking the lever 24 of the joystick 21 or 22 crosswise after selecting "POSITION".

Figure 9A:
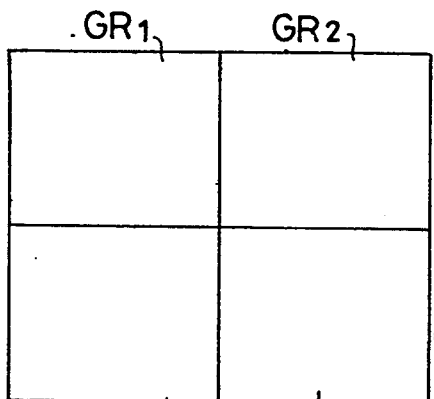
FIGS. 9A through 9C are explanatory views of a "MULT" function.
Figure 9B:
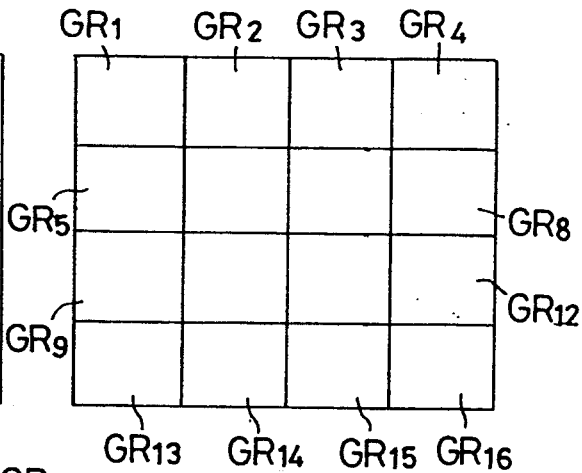
Figure 9C:
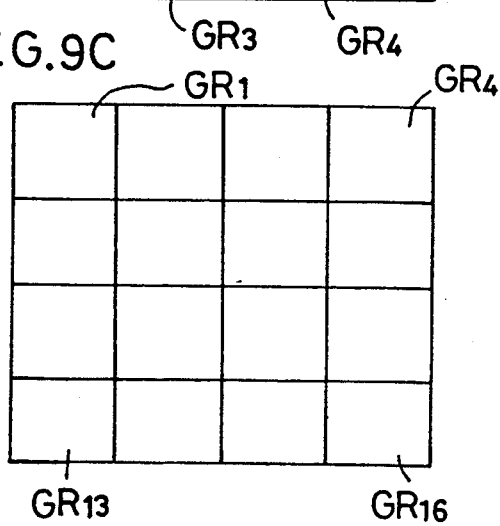
Figure 9C:
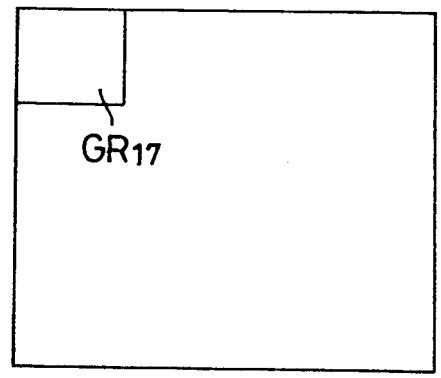

(E) "MULT" is a process of splitting the screen of each reproduced image display monitor 12 or 13 into four or 16 windows for multiple display as shown in FIGS. 9A, 9B and 9C, to display reference images of a plurality of files. Where the same ID has four or less files, the screen is split into four windows as shown in FIG. 9A. Where the same ID has five or more files, the screen is split into 16 windows as shown in FIGS. 9B and 9C. Where the same ID has 17 or more files, a multiscreen mode is employed, with each screen split into 16 windows to display the reference images in the ascending order of the files as shown in FIG. 9C. In FIGS. 9A, 9B and 9C, references $GR_1$–$GR_{17}$ denote reference images of files SUB-ID=1 to 17.

Figure 10:
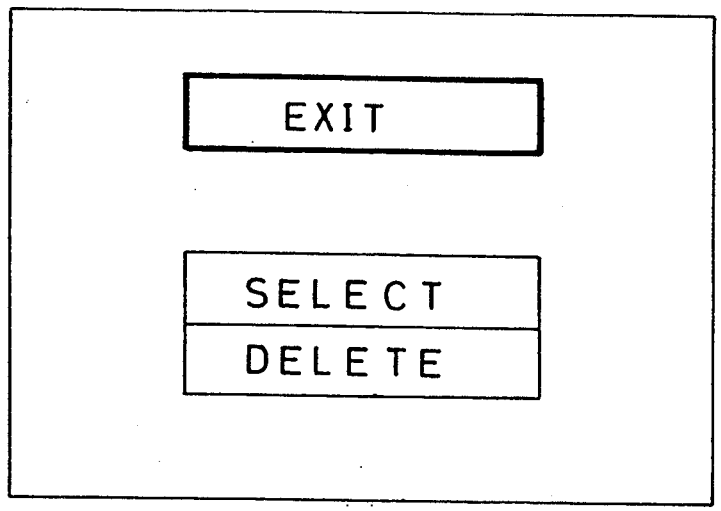
FIG. 10 is a view showing a selector menu of the "MULT" function.

When this function is selected, the second menu displayed on the fluoroscopic image display monitors 15 and 16 is switched to a selector menu of the "MULT"-'function as shown in FIG. 10.

When the menu shown in FIG. 10 is displayed, a bold frame is moved from function to function by rocking the lever 24 of the joystick 21 or 22 backward or forward. A function marked by the bold frame may be selected by pushing the button 25.

(a) "EXIT" is a process of closing this menu and returning to the second menu. Upon selection of "EXIT", the selection of "MULT" is canceled.

Figure 11A:
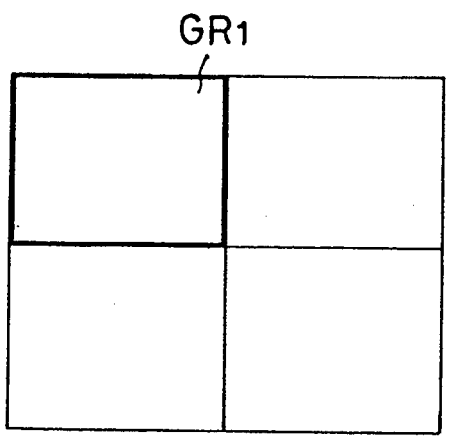
FIGS. 11A through 11D are explanatory views of a file selection by the "MULT" function.
Figure 11B:
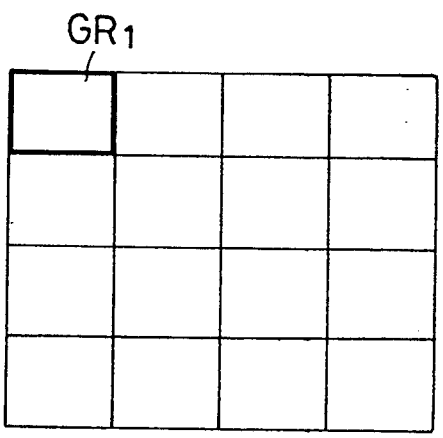
Figure 11C:
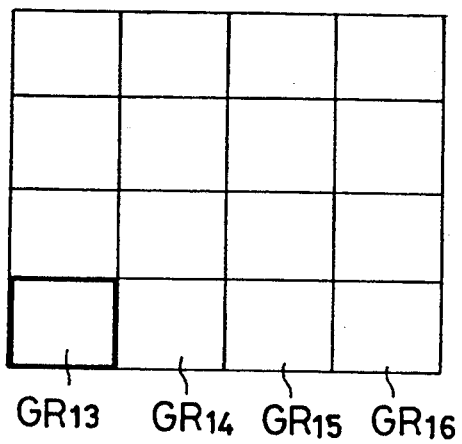
Figure 11D:
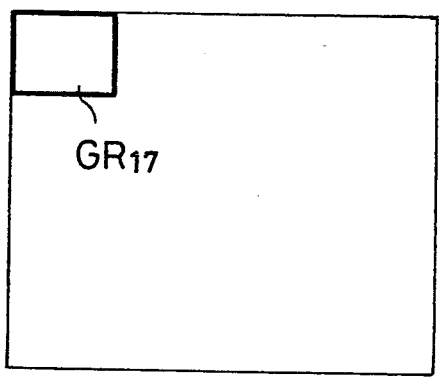

(b) "SELECT" is a process of selecting a file by means of the reference images in the multi-window display on the reproduced image display monitors 12 and 13. When "SELECT" is selected, a bold selector frame appears on one of the reference images displayed on the reproduced image display monitors 12 and 13 as shown in FIGS. 11A and 11B. When, in this state, the lever 14 of the joystick 21 or 22 is rocked crosswise, the bold frame is shifted from image to image. By pressing the button 25, the file containing the reference image marked by the bold frame may be selected. The file selected is reproduced and displayed on the reproduced image display monitors 12 and 13.

Where there are 17 or more files and the reference images are displayed in the multiscreen mode, the bold frame may be moved to the bottom row of images $GR_{13}$ to $GR_{16}$ as shown in FIG. 11C. In this state, the joystick 21 or 22 may be rocked further backward. This operation causes a next screen including the reference images of the 17th and subsequent files as shown in FIG. 11D to appear on the reproduced image display monitors 12 and 13. Similarly, a previous screen may be displayed by shifting the bold frame to the top row of images and rocking the joystick 21 or 22 forward.

(c) "DELETE" is a process of deleting files by means of the reference images in the multi-window display on the reproduced image display monitors 12 and 13. To carry out the "DELETE" function, a bold frame is moved and a reference image is selected as in "SELECT". The file containing the selected reference image is deleted from the magnetic disk unit 11.

In "DELETE" also, as in "SELECT" above, screen switching may be effected on the reproduced image display monitors 12 and 13.

(F) "JUMP" is a process of selecting a file directly by means of the SUB-ID affixed thereto. When this function is selected by operating the joystick 21 or 22, the first menu is displayed on the fluoroscopic image display monitors 15 and 16. The bold frame is shifted by rocking the joystick 21 or 22 backward or forward, and a file indicated by the bold frame is selected by pushing the button 25.

During operation (5) on the first menu, i.e. rocking the joystick 21 or 22 backward or forward and pushing the button 25 to select a file, each time the bold frame is shifted to a different file, the reference image of this file is displayed in still condition on the reproduced image display monitors 12 and 13. In the "JUMP" process, on the other hand, the image displayed on the reproduced image display monitors 12 and 13 is not changed with a shift of the bold frame to a different file. Only when the button 25 is pressed to select the file, a change is made to the image of the selected file. Thus, a file selecting operation by "JUMP" is faster than the above operation (5).

(G) "REF. DISP" is a process of displaying a reference image. When this process is selected by operating the joystick 21 or 22, the reference image of the file currently reproduced is displayed.

(H) "REF. REG" is a process of re-registering a reference image. When this process is selected by operating the joystick 21 or 22, an image currently displayed is registered as the reference image of the file.

(I) "MAP" is a process of calling a load map mode. Load map is a process of displaying currently obtained fluoroscopic images and reproduced radiographic image data in superimposition. When "MAP" is selected by operating the joystick 21 or 22, the image processor 10 causes the reproduced image display monitors 12 and 13 to display currently reproduced radiographic image data as superimposed on fluoroscopic images successively supplied to the image processor 10.

(J) "PROCESS" is a process of setting a magnification ratio, measuring a distance, and measuring a rate of stricture.

Figure 12:
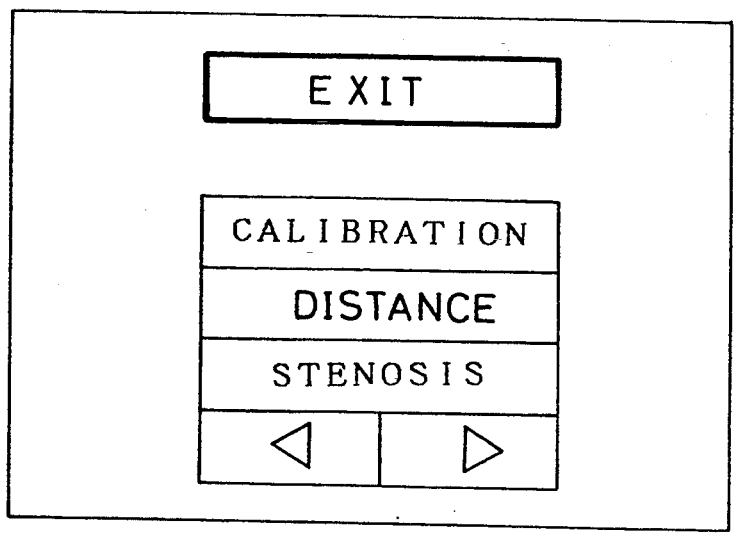
FIG. 12 is a view showing a selector menu of a "PROCESS" function.

When this process is selected, the second menu displayed on the fluoroscopic image display monitors 15 and 16 is replaced by a selector menu of "PROCESS" as shown in FIG. 12.

When the menu shown in FIG. 12 is displayed, a bold frame is moved from function to function by rocking the lever 24 of the joystick 21 or 22 crosswise. A function marked by the bold frame may be selected by pushing the button 25.

(a) "EXIT" is a process of closing this menu and returning to the second menu. Upon selection of "EXIT", the selection of "PROCESS" is canceled.

(b) "◁" and "▷" are used in the "CALIBRATION" process, which represent functions to select an actual size of a catheter inserted into the examinee M. When this function is selected, a change is made in the actual size of the catheter appearing in a catheter size display KJ at the righthand side of each reproduced image display monitor 12 or 13 as shown in FIGS. 7 and 8. The value currently displayed indicates a selected size of the catheter.

Figure 13A:
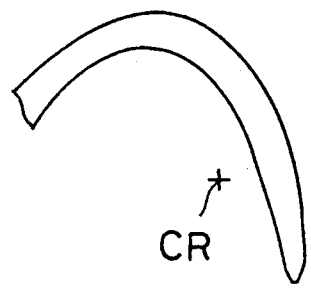
FIGS. 13A and 13B are explanatory views of a magnification ratio selection by the "PROCESS" function.
Figure 13B:
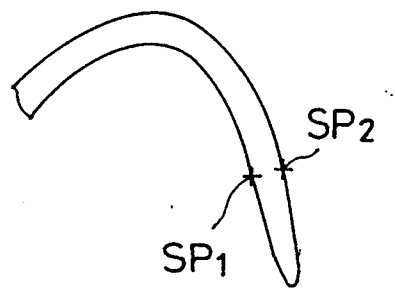

(c) "CALIBRATION" is a process of determining a ratio of one pixel to the actual size of the catheter based on the actual size selected in operation (b) above and a size of the catheter displayed on the reproduced image display monitors 12 and 13. When this process is selected, a cross cursor CR as shown in FIG. 13A appears on the screens. This cursor is moved by rocking the lever 24 of the joystick 21 or 22 crosswise, and specific points are designated by pressing the button 25. Two specific points $SP_1$ and $SP_2$ (at opposite sides of the catheter), as shown in FIG. 13B, are designated by rocking the lever 24 and pressing the button 25 of the joystick 21 or 22. The actual size of the catheter is divided by the number of pixels present between the specific points $SP_1$ and $SP_2$ to determine the size of one pixel of the screen in relation to the actual size of the catheter. FIGS. 13A and 13B are views each showing, as enlarged, a catheter portion of the image displayed on the reproduced image display monitors 12 and 13.

(d) "DISTANCE" is for measuring the thickness of blood vessels, for example, based on the above magnification ratio. When this function is selected, a cursor appears on the screen to enable selection of two distance measuring points as in the point designation for "CALIBRATION" described above. The number of pixels between the two designated points is multiplied by the ratio of one pixel to the actual size determined in "CALIBRATION" above, to obtain an actual distance between the two designated points. Assume, for example, that there are 10 pixels between the two designated points and that one pixel corresponds to 2.3 mm in actual size, the distance between the two designated points is 23 mm in actual size. The result of measurement is displayed in a predetermined righthand position KS on each reproduced image display monitor 12 or 13.

Figure 14:
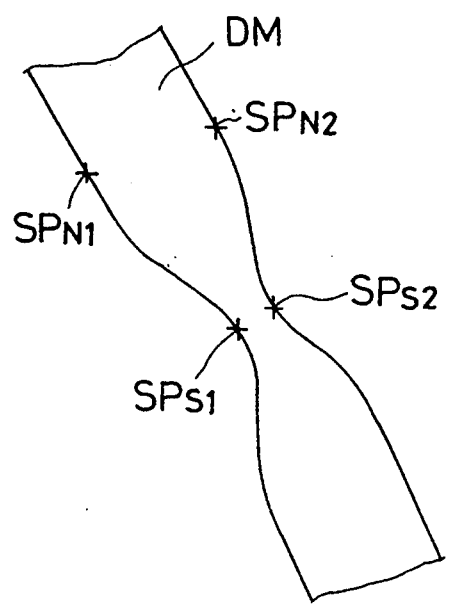
FIG. 14 is an explanatory view of a stricture rate selection by the "PROCESS" function.

(e) "STENOSIS" is for measuring a rate of stenosis in a constricted blood vessel. When this function is selected, a cursor appears on the screen. As in the point designation for "CALIBRATION" described above, the cursor is used to designate, as shown in FIG. 14, two points $SP_{N1}$ and $SP_{N2}$ at opposite sides of a normal portion of a blood vessel, and two points $SP_{S1}$ and $SP_{S2}$ at opposite sides of a constricted portion of the blood vessel. FIG. 14 is an enlarged view of a blood vessel portion of the image displayed on the reproduced image display monitors 12 and 13. A stenosis rate of the constricted portion of the blood vessel may be derived from the number of pixels between points $SP_{S1}$ and $SP_{S2}$ and the number of pixels between points $SP_{N1}$ and $SP_{N2}$. The stenosis rate is shown in percentage, with 100% representing complete clogging of the blood vessel. The result of this computation is displayed in a predetermined righthand position KR on each reproduced image display monitor 12 or 13. This position KR also displays distances between points $SP_{S1}$ and $SP_{S2}$ and between points $SP_{N1}$ and $SP_{N2}$ (with "N" representing the distance between points $SP_{S1}$ and $SP_{S2}$ and "S" between points $SP_{N1}$ and $SP_{N2}$) which are determined in the same way as for "DISTANCE" above.

(K) "ID ↑" and "↓ ID" are a process of changing the IDs. Whenever this process is selected, the IDs are changed and the radiographic image data of a selected ID are displayed on the reproduced image display monitors 12 and 13.

The contents of the menus displayed on the fluoroscopic image display monitors 15 and 16 are not limited to the first and second menus described above. The menus may include other processes or functions.

Figure 15:
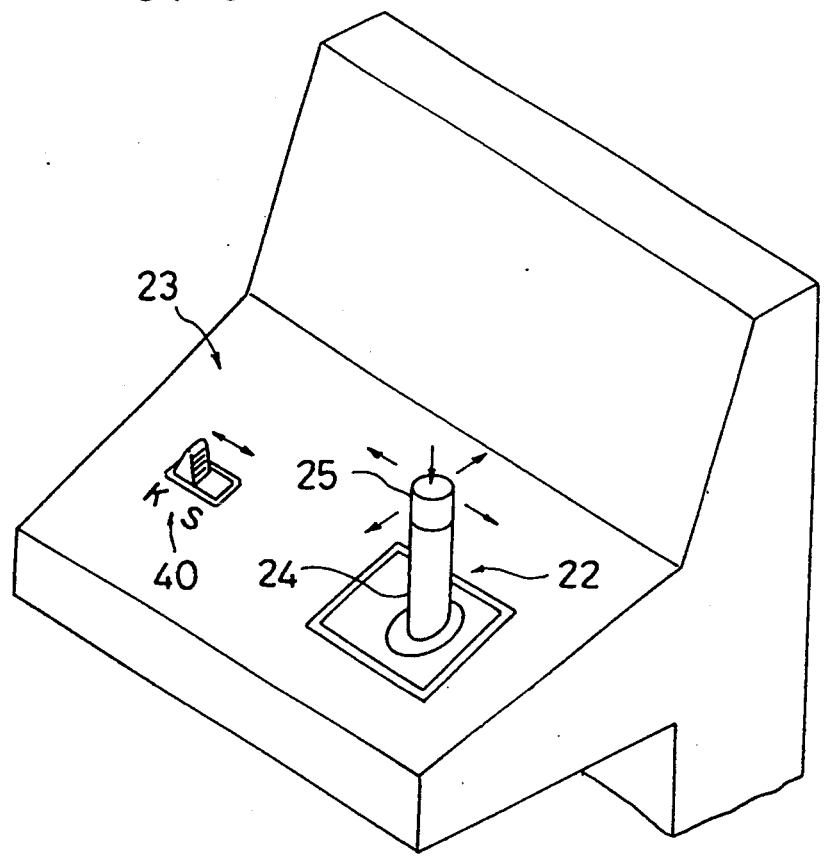
FIG. 15 is a perspective view of a changeover switch on a control console (for enabling or setting an order of priority of the joysticks)

The joysticks 21 and 22 are independently operable to effect the various operations (such as the operations on the first menu and those on the second menu), i.e. by the operator and the engineer independently of each other.

Where an integration of such operations is desired, a switching function may be provided to enable only one of the joysticks 21 and 22. As shown in FIG. 15, for example, the control console 23 may include a changeover switch 40. When the changeover switch 40 is set to "K", the controller 20 accepts operations only from the joystick 21 installed in the examination room KS. When the changeover switch 40 is set to "S", the controller 20 accepts instructions only from the joystick 22 installed in the control room SS.

An order of priority may be given to the joysticks 21 and 22 in case the operations thereof overlap. As shown in FIG. 15, for example, the control console 23 may include a changeover switch 40. When the operations of the joysticks 21 and 22 overlap, the controller 20 may accept instructions only from the joystick 21 or 22 to which priority is given. When, for example, the changeover switch 40 is set to "K", priority is given to the joystick 21 installed in the examination room KS. When the changeover switch 40 is set to "S", priority is given to the joystick 22 installed in the control room SS.

The controls based on the enable switching or the order of priority of these joysticks 21 and 22 may be employed likewise in the other embodiments described later.

In this and other embodiments, the control room SS also includes the joystick 22, reproduced image display monitor 13 and fluoroscopic image display monitor 16 to allow the engineer as well as the operator to carry out the radiographic image data selecting and other operations.

However, it is adequate if at least the operator can effect the radiographic image data selecting and other operations in the examination room KS during an IVR procedure. Thus, the joystick 22, reproduced image display monitor 13 and fluoroscopic image display monitor 16 in the control room SS are dispensable.

Operations for observing fluoroscopic images will be described next.

When the operator adjusts an angular relationship between the examinee M and the X-ray tube 2 and depresses the monitoring foot switch 6 to observe X-ray pictures, the X-ray tube 2 emits X-rays. The X-rays having penetrated the examinee M are transmitted through the image intensifier unit 3, television camera 7, CCU 8 and A/D converter 9 to the image processor 10. Since the monitoring foot switch 6 is depressed at this time, the input terminal "a" of the switch 18 is selected. Consequently, fluoroscopic images are transmitted from the image processor 10 through the A/D converter 17 to the fluoroscopic image display monitors 15 and 16 to be displayed thereon. The menus from the GC 18 are not displayed at this time, as noted hereinbefore.

Operations carried out by the operator (or engineer) during an IVR procedure will be described next.

In the IVR procedure, the operator operates the joystick 21 (or the engineer operates the joystick 22) to select desired radiographic image data. Then, the operator steps on the monitoring foot switch 6 to cause fluoroscopic images of the examinee M to be displayed on the fluoroscopic image display monitor 15 (16). The operator conducts the IVR procedure while referring also to the radiographic image data reproduced on the reproduced image display monitor 12 (13). Changes of the radiographic image data (files) and reproducing speeds may be effected at this time through the joystick 21 (22). It is also possible to release the monitoring foot switch 6 once, as necessary, to switch the fluoroscopic image display monitor 15 (16) to a menu screen and select a desired process from the second menu, e.g. display the radiographic image data in enlargement.

In the examination room, the reproduced image display monitor 12 and fluoroscopic image display monitor 15 should desirably be arranged adjacent each other. With these monitors 12 and 15 arranged adjacent each other, the operator may operate the joystick 21 without looking away from the monitors. This provides improved operating efficiency.

Figure 16:
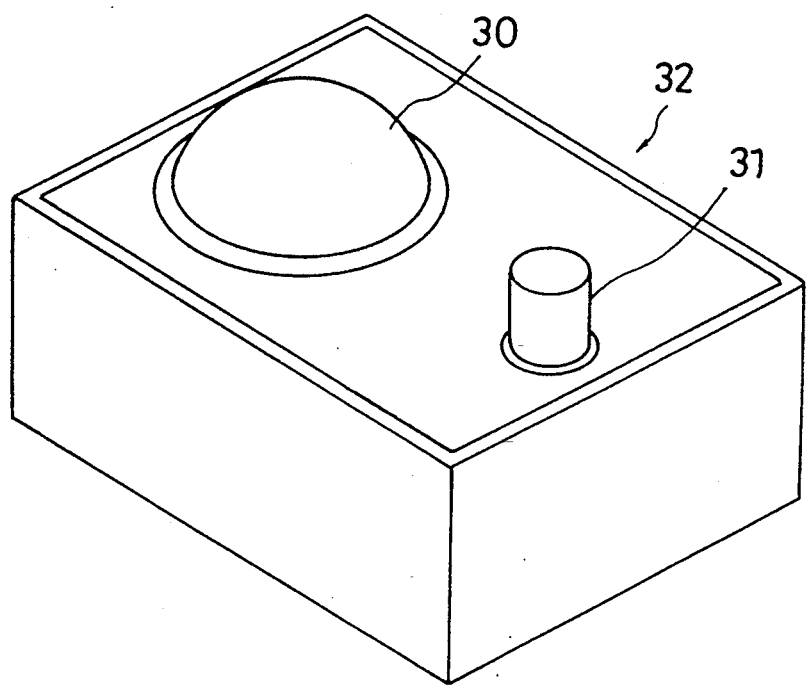
FIG. 16 is a perspective view of a modified selecting and instructing device.

In the above and subsequent embodiments, the joysticks 21 and 22 are used as the selecting and instructing device. As shown in FIG. 16, for example, a trackball 30 and a pushbutton 31 may constitute a unit to act as a selecting and instructing device 32. In this case, the trackball 30 provides a replacement for the crosswise rocking of the lever 24 of the joystick 21 or 22, while the pushbutton 31 provides a replacement for the operation of the button 25 of the joystick 21 or 22.

In the foregoing embodiment, the switching between fluoroscopic images and menus on the fluoroscopic image display monitors 15 and 16 is effected through the switch 19 based on whether the monitoring foot switch 6 is depressed or not. For example, switching may be made to superimpose the menus on the fluoroscopic images displayed.

Figure 17:
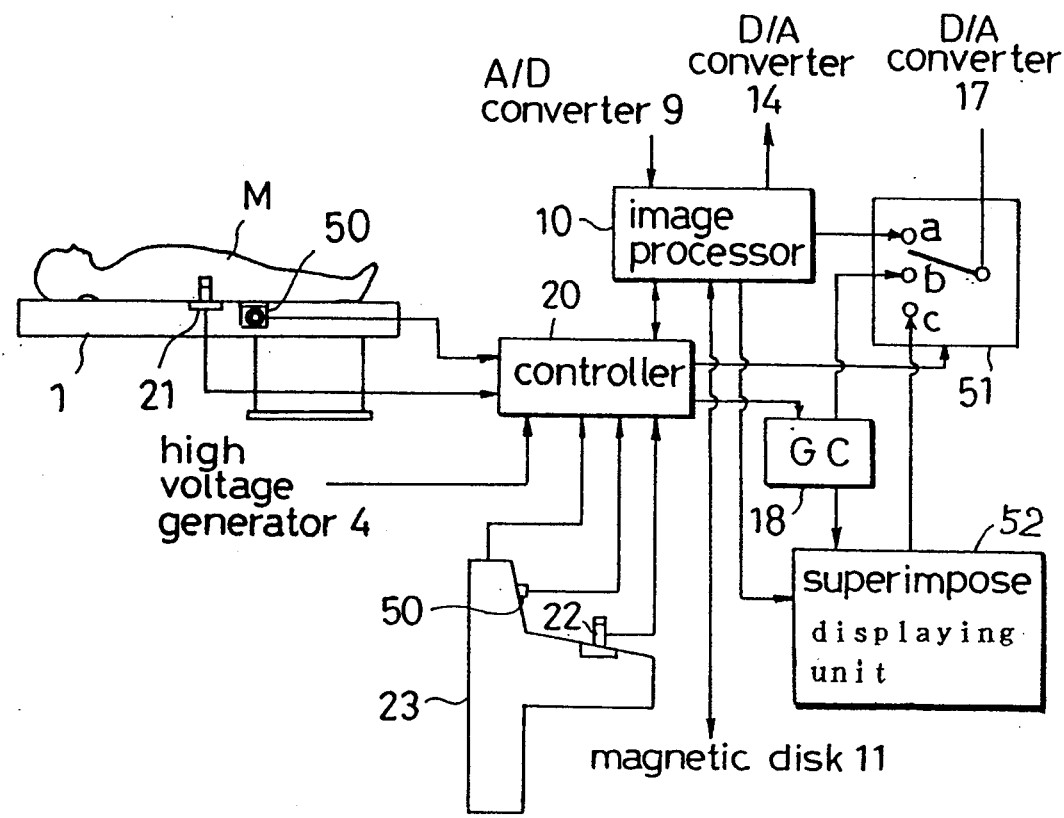
FIG. 17 is a block diagram showing a modified principal portion of the first embodiment.

This aspect will be described with reference to FIG. 17. FIG. 17 shows a modified portion of the apparatus shown in FIG. 1. The components omitted from FIG. 17 are the same as in FIG. 1. In the illustrated modification, display changeover switches 50 are disposed, for example, adjacent the joystick 21 in the examination room KS, and on the control console 23 in the control room SS, respectively. These display changeover switches 50 are operable for switching between ordinary display and superimpose display. Each display changeover switch 50 is in the form of a pushbutton switch. With each depression of this button, switching is made between ordinary display and superimpose display.

Figure 18:
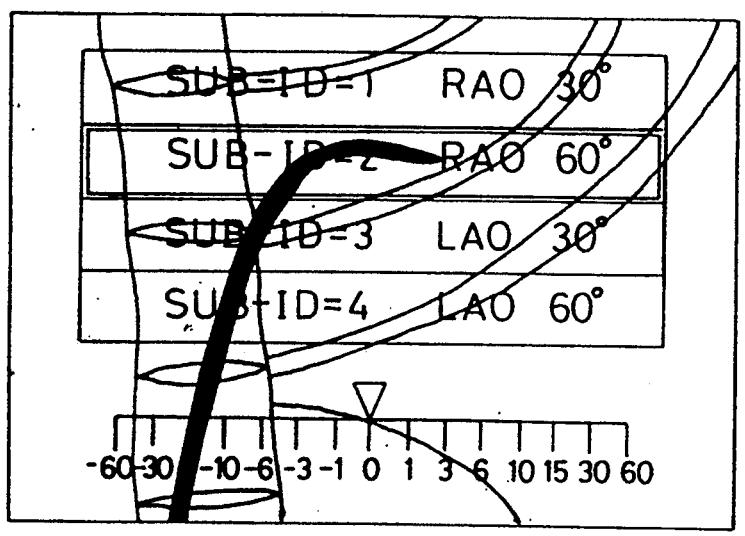
FIG. 18 is a view showing a menu superimposed on a fluoroscopic image.

The output data (fluoroscopic images) of the image processor 10 are inputted to an input terminal "a" of a switch 51, while the menu display data generated by the GC 18 are inputted to an input terminal "b" thereof. Further, an input terminal "c" receives display data, generated by the superimpose displaying unit 52, of screens showing a menu superimposed on fluoroscopic images (see FIG. 18).

The controller 20 operates the switch 51 in response to a state of the display changeover switch 50 and a state of the monitoring foot switch 6.

That is, when the display changeover switch 50 is in a state for ordinary display, the input terminal "a" or "b" of the switch 50 is selected according to a state of the monitoring foot switch 6 as in the foregoing embodiment. At this time, either the fluoroscopic images or the menus are displayed on the fluoroscopic image display monitors 15 and 16, depending on the state of the monitoring foot switch 6.

When the display changeover switch 50 is in a state for superimpose display, the input terminal "c" of the switch 50 is selected regardless of a state of the monitoring foot switch 6. Then, the fluoroscopic images and menus are displayed in superimposition on the fluoroscopic image display monitors 15 and 16. Since the menus are displayed at this time, the operations of the joystick 21 or 22 according to the menus are accepted as valid.

With this construction, the operator may select processes according to the menus during the IVR procedure, by operating the joystick 21, while observing the fluoroscopic images displayed.

In the above construction, one of the display changeover switches 50 is provided on the control console 23. However, this display changeover switch 50 may be omitted from the control console 23 since only the operator may effect the switching operations during the IVR procedure.

The above display changeover switches 50 correspond to a display switching instructing device of this invention. The superimpose displaying unit 52 corresponds to a superimposing device of this invention.

Second Embodiment

Figure 19:
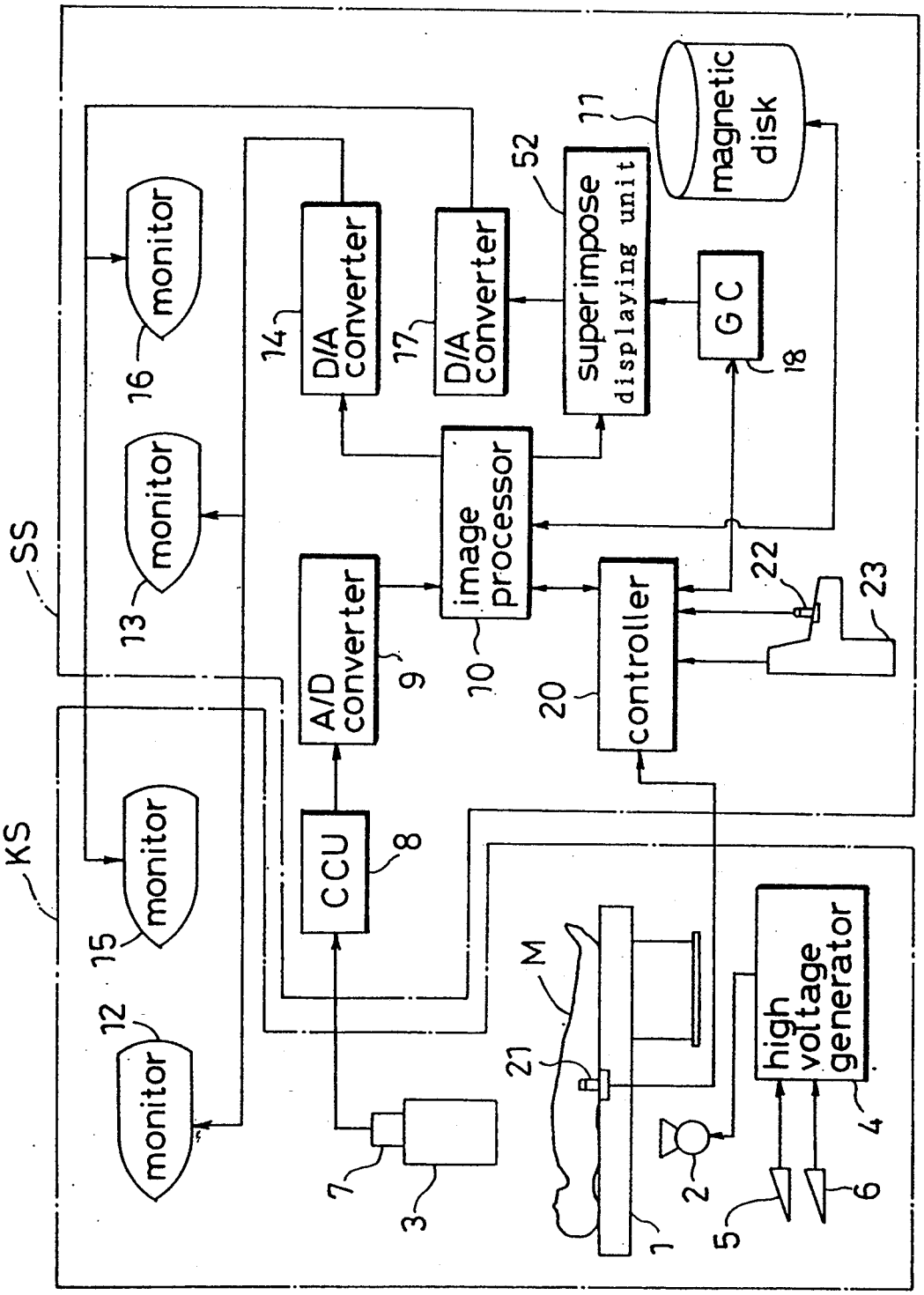
FIG. 19 is a block diagram showing a second embodiment of this invention.

FIG. 19 is a block diagram showing an outline of a digital radiographic apparatus in a second embodiment of this invention. In FIG. 19, like references are used to identify like parts in FIG. 1 which are the same as in the first embodiment and will not particularly be described again.

The second embodiment includes a superimpose displaying unit 52 (superimposing device) in place of the switch 19 (display switching device) in the first embodiment. Thus, the fluoroscopic image display monitors 15 and 16 display the menus generated by the GC 18 as superimposed on currently obtained fluoroscopic images (see FIG. 18).

With this construction, the first or second menu generated by the GC 18 is constantly displayed on the fluoroscopic image display monitors 15 and 16 as superimposed on the fluoroscopic images throughout the IVR procedure. Consequently, the operator may, at any time during the IVR procedure, select radiographic image data and display modes by operating the joystick 21, while fluoroscopic images are displayed on the fluoroscopic image display monitor 15. The engineer may also select radiographic image data and display modes at any time by operating the joystick 22 according to the menus displayed on the fluoroscopic image display monitor 16.

The GC 18 in this embodiment corresponds to the menu generating means in claim 2.

Third Embodiment

Figure 20:
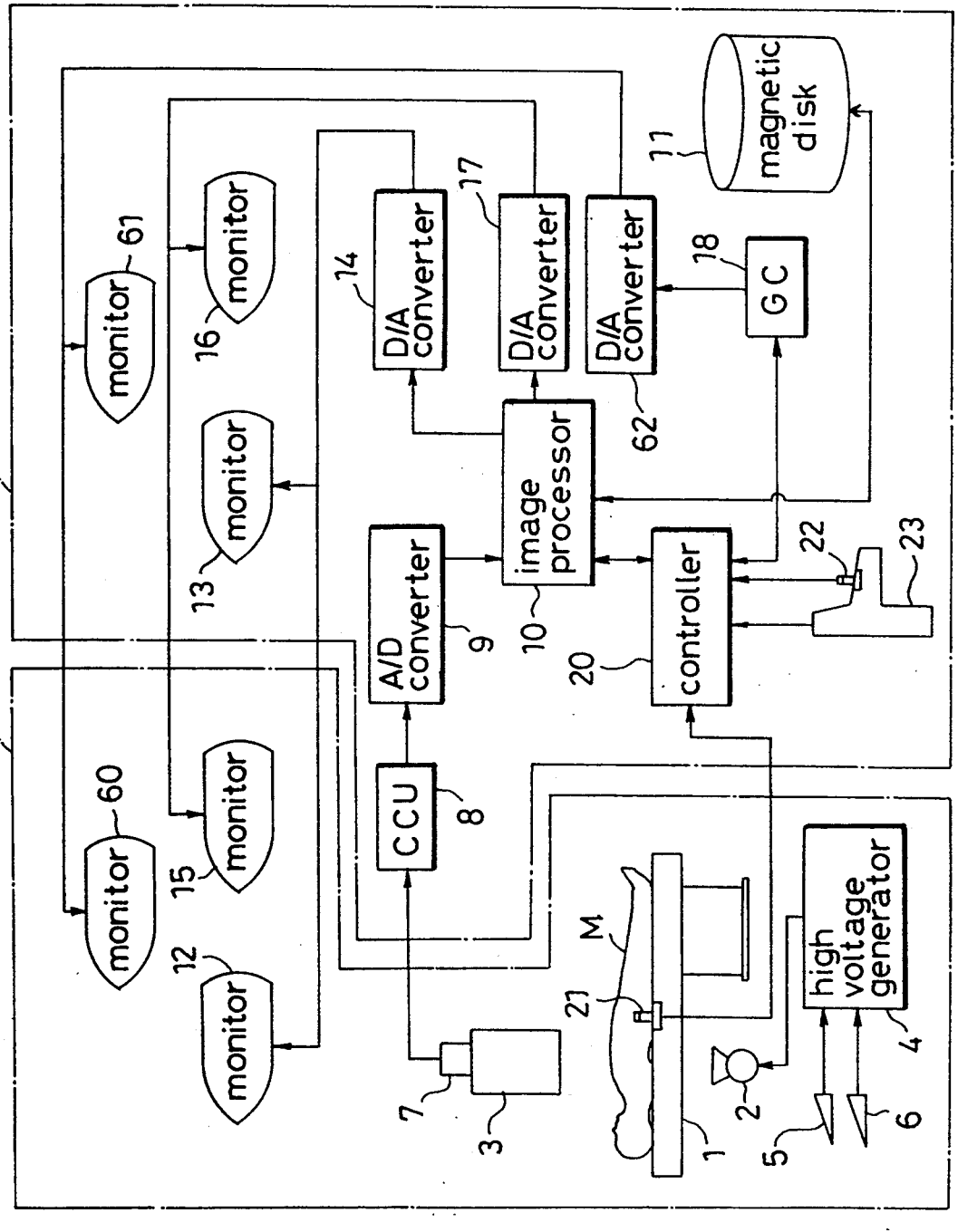
FIG. 20 is a block diagram showing a third embodiment of this invention.

FIG. 20 is a block diagram showing an outline of a digital X-ray radiographic apparatus in a third embodiment of this invention. In FIG. 20, like references are used to identify like parts in FIG. 1 which are the same as in the first embodiment and will not particularly be described again.

The third embodiment dispenses with the switch 19 (display switching device) in the first embodiment, and includes menu display monitors 60 and 61 besides the fluoroscopic image display monitors 15 and 16. The menus generated by the GC 18 are transmitted through a D/A converter 62 to the menu display monitors 60 and 61 to be displayed thereon. The menu display monitor 60 is installed in the examination room, and the menu display monitor 61 in the control room. In this embodiment, the menu display monitor 60 corresponds to a menu display monitor of this invention installed in the examination room, and the menu display monitor 61 to a control room menu display monitor of this invention installed in the control room.

With this construction, the first or second menu generated by the GC 18 is displayed on the menu display monitors 60 and 61 during the IVR procedure. Consequently, the operator may, during the IVR procedure, select radiographic image data and display modes by referring to the menu displayed on the menu display monitor 60 and operating the joystick 21.

In the examination room, the menu display monitor 60 should desirably be disposed adjacent the reproduced image display monitor 12 and fluoroscopic image display monitor 15. With these monitors 12, 15 and 60 arranged adjacent one another, the operator may operate the joystick 21 without looking away from the monitors. This provides improved operating efficiency.

The menu display monitor 61 in the control room is dispensable, as are the reproduced image display monitor 13 and fluoroscopic image display monitor 16.

In each of the embodiments described hereinbefore, the same construction is employed for displaying the menus in the control room as for displaying the menus in the examination room. However, such construction may be differentiated for each room.

In the third embodiment, for example, the reproduced image display monitor 13 and fluoroscopic image display monitor 16 may be installed in the control room. In this case, the fluoroscopic image display monitor 16 may be used to display the menus superimposed on the fluoroscopic images.

The present invention may be embodied in other specific forms without departing from the spirit or essential attributes thereof and, accordingly, reference should be made to the appended claims, rather than to the foregoing specification, as indicating the scope of the invention.

What is claimed is:

1. A digital X-ray radiographic apparatus for digitalizing and collecting X-ray penetration images of an examinee, and reproducing the X-ray penetration images collected, said apparatus comprising:

X-ray penetrating means for obtaining the X-ray penetration images from the examinee;

signal converting means for digitalizing the X-ray penetration images received from said X-ray penetrating means;

storage means for storing the X-ray penetration images digitalized by said signal converting means;

a reproduced image display monitor installed in an examination room along with said X-ray penetrating means, for reproducing and displaying the X-ray penetration images (hereinafter referred to as "radiographic image data") digitalized and stored in said storage means;

a fluoroscopic image display monitor installed in said examination room for displaying fluoroscopic images being picked up by said X-ray penetrating means;

menu generating/displaying means for generating a menu including at least a function to select radiographic image data to be reproduced and displayed on said reproduced image display monitor, and causing said menu to be displayed on said fluoroscopic image display monitor;

selecting and instructing means installed in said examination room for selecting and instructing functions shown on said menu;

display switching means for switching said fluoroscopic image display monitor between a state for displaying said fluoroscopic images being picked up by said X-ray penetrating means and a state for displaying said menu generated by said menu generating/displaying means; and control means responsive to instructions received from said selecting and instructing means for causing the radiographic image data to be reproduced and displayed on said reproduced image display monitor.

2. A digital X-ray radiographic apparatus for digitalizing and collecting X-ray penetration images of an examinee, and reproducing the X-ray penetration images collected, said apparatus comprising:

X-ray penetrating means for obtaining the X-ray penetration images from the examinee;

signal converting means for digitalizing the X-ray penetration images received from said X-ray penetrating means;

storage means for storing the X-ray penetration images digitalized by said signal converting means;

a reproduced image display monitor installed in an examination room along with said X-ray penetrating means, for reproducing and displaying the X-ray penetration images (hereinafter referred to as "radiographic image data") digitalized and stored in said storage means;

a fluoroscopic image display monitor installed in said examination room for displaying fluoroscopic images being picked up by said X-ray penetrating means;

menu generating means for generating a menu including at least a function to select radiographic image data to be reproduced and displayed on said reproduced image display monitor;

superimposing means for causing said menu to be displayed on said fluoroscopic image display monitor in superimposition on said fluoroscopic images being picked up by said X-ray penetrating means;

selecting and instructing means installed in said examination room for selecting and instructing functions shown on said menu; and control means responsive to instructions received from said selecting and instructing means for causing the radiographic image data to be reproduced and displayed on said reproduced image display monitor.

3. A digital X-ray radiographic apparatus for digitalizing and collecting X-ray penetration images of an examinee, and reproducing the X-ray penetration images collected, said apparatus comprising:

X-ray penetrating means for obtaining the X-ray penetration images from the examinee;

signal converting means for digitalizing the X-ray penetration images received from said X-ray penetrating means;

storage means for storing the X-ray penetration images digitalized by said signal converting means;

a reproduced image display monitor installed in an examination room along with said X-ray penetrating means, for reproducing and displaying the X-ray penetration images (hereinafter referred to as "radiographic image data") digitalized and stored in said storage means;

a fluoroscopic image display monitor installed in said examination room for displaying fluoroscopic images being picked up by said X-ray penetrating means;

a menu display monitor installed in said examination room;

menu generating/displaying means for generating a menu including at least a function to select radiographic image data to be reproduced and displayed on said reproduced image display monitor, and causing said menu to be displayed on said menu display monitor;

selecting and instructing means installed in said examination room for selecting and instructing functions shown on said menu; and control means responsive to instructions received from said selecting and instructing means for causing the radiographic image data to be reproduced and displayed on said reproduced image display monitor.

4. A digital X-ray radiographic apparatus as defined in claim 1, further comprising:

superimposing means for causing said menu to be displayed on said fluoroscopic image display monitor in superimposition on said fluoroscopic images being picked up by said X-ray penetrating means; and display switching instructing means for instructing said superimposing means, when one of the fluoroscopic images picked up by said X-ray penetrating means and said menu generated by said menu generating/displaying means is displayed on said penetration image display monitor, to switch to a state for displaying said menu in superimposition on said fluoroscopic images;

wherein said display switching means has a function responsive to instructions from said display switching instructing means to switch said fluoroscopic image display monitor to a state for displaying said menu in superimposition on said fluoroscopic images under control of said superimposing means.

5. A digital X-ray radiographic apparatus as defined in claim 1, wherein said selecting and instructing means is a joystick having a pushbutton.

6. A digital X-ray radiographic apparatus as defined in claim 2, wherein said selecting and instructing means is a joystick having a pushbutton.

7. A digital X-ray radiographic apparatus as defined in claim 3, wherein said selecting and instructing means is a joystick having a pushbutton.

8. A digital X-ray radiographic apparatus as defined in claim 1, wherein:

said menu generated by said menu generating/displaying means includes, besides the function to select radiographic image data to be reproduced and displayed on said reproduced image display monitor, a function to select a display mode for displaying said radiographic image data on said reproduced image display monitor;

said selecting and instructing means is operable to select and instruct the functions shown on said menu; and said control means is operable to cause the radiographic image data to be reproduced and displayed on said reproduced image display monitor in response to the functions selected by said selecting and instructing means.

9. A digital X-ray radiographic apparatus as defined in claim 2, wherein:

said menu generated by said menu generating means includes, besides the function to select radiographic image data to be reproduced and displayed on said reproduced image display monitor, a function to select a display mode for displaying said radiographic image data on said reproduced image display monitor;

said selecting and instructing means is operable to select and instruct the functions shown on said menu; and said control means is operable to cause the radiographic image data to be reproduced and displayed on said reproduced image display monitor in response to the functions selected by said selecting and instructing means.

10. A digital X-ray radiographic apparatus as defined in claim 3, wherein:

said menu generated by said menu generating means includes, besides the function to select radiographic image data to be reproduced and displayed on said reproduced image display monitor, a function to select a display mode for displaying said radiographic image data on said reproduced image display monitor;

said selecting and instructing means is operable to select and instruct the functions shown on said menu; and said control means is operable to cause the radiographic image data to be reproduced and displayed on said reproduced image display monitor in response to the functions selected by said selecting and instructing means.

11. A digital X-ray radiographic apparatus as defined in claim 1, further comprising:

a control room reproduced image display monitor installed in a control room provided separately from said examination room, for reproducing and displaying the X-ray penetration images stored in said storage means;

a control room menu display monitor installed in said control room for displaying said menu; and control room selecting and instructing means installed in said control room for selecting and instructing functions shown on said menu displayed on said control room menu display monitor;

wherein said control means is operable to cause the radiographic image data to be reproduced and displayed on said reproduced image display monitor and said control room reproduced image display monitor in response to instructions received from one of said selecting and instructing means and said control room selecting and instructing means.

12. A digital X-ray radiographic apparatus as defined in claim 2, further comprising:

a control room reproduced image display monitor installed in a control room provided separately from said examination room, for reproducing and displaying the X-ray penetration images stored in said storage means;

a control room menu display monitor installed in said control room for displaying said menu; and control room selecting and instructing means installed in said control room for selecting and instructing functions shown on said menu displayed on said control room menu display monitor;

wherein said control means is operable to cause the radiographic image data to be reproduced and displayed on said reproduced image display monitor and said control room reproduced image display monitor in response to instructions received from one of said selecting and instructing means and said control room selecting and instructing means.

13. A digital X-ray radiographic apparatus as defined in claim 3, further comprising:

a control room reproduced image display monitor installed in a control room provided separately from said examination room, for reproducing and displaying the X-ray penetration images stored in said storage means;

a control room menu display monitor installed in said control room for displaying said menu; and control room selecting and instructing means installed in said control room for selecting and instructing functions shown on said menu displayed on said control room menu display monitor;

wherein said control means is operable to cause the radiographic image data to be reproduced and displayed on said reproduced image display monitor and said control room reproduced image display monitor in response to instructions received from one of said selecting and instructing means and said control room selecting and instructing means.

14. A digital X-ray radiographic apparatus as defined in claim 11, further comprising priority setting means for setting an order of priority for said selecting and instructing means installed in said examination room and said control room selecting and instructing means installed in said control room, wherein said control means is operable to cause the radiographic image data to be reproduced and displayed on said reproduced image display monitor and said control room reproduced image display monitor in response to instructions received from one of said selecting and instructing means and said control room selecting and instructing means, whichever is given priority by said priority setting means, when said selecting and instructing means and said control room selecting and instructing means transmit overlapping instructions.

15. A digital X-ray radiographic apparatus as defined in claim 12, further comprising priority setting means for setting an order of priority for said selecting and instructing means installed in said examination room and said control room selecting and instructing means installed in said control room, wherein said control means is operable to cause the radiographic image data to be reproduced and displayed on said reproduced image display monitor and said control room reproduced image display monitor in response to instructions received from one of said selecting and instructing means and said control room selecting and instructing means, whichever is given priority by said priority setting means, when said selecting and instructing means and said control room selecting and instructing means transmit overlapping instructions.

16. A digital X-ray radiographic apparatus as defined in claim 13, further comprising priority setting means for setting an order of priority for said selecting and instructing means installed in said examination room and said control room selecting and instructing means installed in said control room, wherein said control means is operable to cause the radiographic image data to be reproduced and displayed on said reproduced image display monitor and said control room reproduced image display monitor in response to instructions received from one of said selecting and instructing means and said control room selecting and instructing means, whichever is given priority by said priority setting means, when said selecting and instructing means and said control room selecting and instructing means transmit overlapping instructions.

17. A digital X-ray radiographic apparatus as defined in claim 11, further comprising validity selecting means for selecting, as valid, instructions from only one of said selecting and instructing means installed in said examination room and said control room selecting and instructing means installed in said control room, wherein said control means is operable to cause the radiographic image data to be reproduced and displayed on said reproduced image display monitor and said control room reproduced image display monitor in response to the instructions received from one of said selecting and instructing means and said control room selecting and instructing means, whichever is selected as valid by said validity selecting means.

18. A digital X-ray radiographic apparatus as defined in claim 12, further comprising validity selecting means for selecting, as valid, instructions from only one of said selecting and instructing means installed in said examination room and said control room selecting and instructing means installed in said control room, wherein said control means is operable to cause the radiographic image data to be reproduced and displayed on said reproduced image display monitor and said control room reproduced image display monitor in response to the instructions received from one of said selecting and instructing means and said control room selecting and instructing means, whichever is selected as valid by said validity selecting means.

19. A digital X-ray radiographic apparatus as defined in claim 13, further comprising validity selecting means for selecting, as valid, instructions from only one of said selecting and instructing means installed in said examination room and said control room selecting and instructing means installed in said control room, wherein said control means is operable to cause the radiographic image data to be reproduced and displayed on said reproduced image display monitor and said control room reproduced image display monitor in response to the instructions received from one of said selecting and instructing means and said control room selecting and instructing means, whichever is selected as valid by said validity selecting means.

* * * * *